(12) United States Patent
Yan et al.

(10) Patent No.: US 9,322,759 B2
(45) Date of Patent: Apr. 26, 2016

(54) VIBRATING TUBE DENSITOMETERS

(75) Inventors: Tinghu Yan, Uxbridge (GB); George Macdonald, Wokingham (GB); David Malcolm Campbell, Lewes (GB)

(73) Assignee: Mobrey Limited, Berkshire (GB)

( * ) Notice: Subject to any disclaimer, the term of this patent is extended or adjusted under 35 U.S.C. 154(b) by 706 days.

(21) Appl. No.: 13/576,806

(22) PCT Filed: Feb. 4, 2011

(86) PCT No.: PCT/GB2011/000154
§ 371 (c)(1),
(2), (4) Date: Aug. 2, 2012

(87) PCT Pub. No.: WO2011/095784
PCT Pub. Date: Aug. 11, 2011

(65) Prior Publication Data
US 2012/0310579 A1    Dec. 6, 2012

(30) Foreign Application Priority Data
Feb. 6, 2010 (GB) .................................. 1001948.7

(51) Int. Cl.
*G01N 9/00* (2006.01)

(52) U.S. Cl.
CPC ...................... *G01N 9/002* (2013.01)

(58) Field of Classification Search
CPC .................. G01N 9/002; G01N 9/36
See application file for complete search history.

(56) References Cited

U.S. PATENT DOCUMENTS

| | | | |
|---|---|---|---|
| 4,872,351 A | 10/1989 | Ruesch | |
| 2002/0184940 A1* | 12/2002 | Storm et al. | 73/32 A |
| 2003/0200816 A1* | 10/2003 | Francisco, Jr. | 73/861.18 |
| 2004/0123645 A1 | 7/2004 | Storm, Jr. et al. | |
| 2007/0186684 A1 | 8/2007 | Pham | 73/861.357 |
| 2008/0257066 A1* | 10/2008 | Henry et al. | 73/861.356 |

FOREIGN PATENT DOCUMENTS

| | | |
|---|---|---|
| EP | 1 306 659 A2 | 5/2003 |
| GB | 2 062 865 A | 5/1981 |
| WO | WO 2005/040733 A1 | 9/2003 |
| WO | 2005003690 A2 | 1/2005 |
| WO | 2005010467 A2 | 2/2005 |
| WO | WO 2006/009548 | 1/2006 |

OTHER PUBLICATIONS

Charles S. Oakes et al. "Apparent Molar Volumes of Aqueous Calcium Chloride to 250° C., 400 bars, and from Molalities of 0.242 to 6.150", Journal of Solution Chemistry, vol. 24, No. 9, 1995, pp. 897-916.*
International Search Report from PCT/GB2011/000154, dated Jun. 15, 2011.
Search Report for GB Application No. GB1001948.7, dated Apr. 22, 2010, 1 page.

* cited by examiner

*Primary Examiner* — Alexander Satanovsky
(74) *Attorney, Agent, or Firm* — Westman, Champlin & Koehler, P.A.

(57) ABSTRACT

The invention provides a method of calibrating a vibrating tube densitometer intended to operate at combined elevated temperatures and pressures.

2 Claims, 4 Drawing Sheets

New performace with $K_{22}$ and $K_{23}$ on a fluid of base density 826.8 $kgm^{-3}$ at combined temperature and pressure conditions New performace with $K_{22}$ and $K_{23}$ on a fluid of base density 914.0 $kgm^{-3}$ at combined temperature and pressure conditions

VIBRATING TUBE DENSITOMETERS

CROSS-REFERENCE TO RELATED APPLICATION

This Application is a Section 371 National Stage Application of International Application No. PCT/GB2011/000154, filed 4 Feb. 2011 and published as WO 2011/095784 on Aug. 11, 2011, in English, the contents of which are hereby incorporated by reference in their entirety.

FIELD OF THE INVENTION

This invention relates to vibrating tube densitometers.

BACKGROUND TO THE INVENTION

Vibrating tube densitometers are a well-known form of apparatus for measuring the density of a flowing medium. One example of this form of apparatus is described in British Patent 2 062 865.

In operation, a vibrating tube densitometer is excited so as to vibrate, in a particular mode, at its resonant frequency. This resonant frequency will be effected by changes in the density of the fluid contained in, or passing through, the tube. The indicated density will also be effected by the fluid temperature and/or fluid pressure to which the vibrating tube is subjected.

This requires each densitometer to be calibrated as can be more readily understood with reference to the following:

The resonant frequency of a vibrating tube densitometer with fluid contained in it can be expressed as:

$$f = \frac{1}{2\pi}\sqrt{\frac{k}{m_r + V_f \cdot \rho_f}} \quad \text{(Equation 1)}$$

where
- f is the resonant frequency of the vibrating tube densitometer containing a fluid
- $m_r$ is the mass of the resonant element within the vibrating tube densitometer
- $V_f$ is the volume of the fluid contained in the resonant element
- $\rho_f$ is the density of the fluid contained in the resonant element
- k is the stiffness of the resonant element Among the above parameters, $m_r$ is a constant. All the other parameters vary with measurement conditions, i.e. mainly temperature (t) and pressure (p), therefore we have $V_f(t, p)$, $\rho_f(t, p)$, $k(t, p)$–fluid volume, fluid density and resonant element stiffness as functions of temperature and pressure respectively.

At measurement conditions, the resonant frequency (f) of a vibrating tube densitometer containing a fluid, varies with not only the fluid density $\rho_f(t,p)$, but also with the volume of the fluid $V_f(t, p)$ and the stiffness of the resonant element $k(t, p)$ which both are affected by the temperature/pressure effects of the vibrating tube densitometer.

Equation 1 can be rewritten in terms of fluid density as:

$$\rho_f = K_0 + K_2 \tau^2 \quad \text{(Equation 2)}$$

where $K_0 = -m_r/V_f$, $K_2 = k/(4\pi^2 V_f)$, and $\tau = 1/f$ is the period of oscillation.

As Equation 1 is only a first order approximation to the actual behavior of a vibrating tube densitometer containing a fluid, more generic equations have been developed for use in the calibration of specific vibration tube densitometers.

One example of such a generic equation is:

$$D = K_0 + K_1 \cdot \tau + K_2 \cdot \tau^2 \quad \text{(Equation 3)}$$

in which $K_0$, $K_1$, and $K_2$ are density coefficients to be calibrated, D is the indicated fluid density, and $\tau$ is the period of oscillation.

One way to calibrate such a densitometer is to determine $K_0$, $K_1$, and $K_2$, across the full operational temperature and pressure range, with fluids of known density at those conditions. The relationships between $K_0$, $K_1$, $K_2$, and temperature and pressure, can then be derived. This method requires numerous calibration points.

One more conventional way to calibrate such a densitometer is to first determine density coefficients $K_0$, $K_1$, and $K_2$ at a reference temperature and pressure condition, such as at temperature $t_0 = 20°$ C. and at atmospheric pressure $p_0 = 1$ BarA; then determine the temperature effects of the densitometer at the reference pressure condition; and then determine the pressure effects of the densitometer at the reference temperature condition. In other words, the temperature effects of densitometer are calibrated at the reference pressure condition and the pressure effects of densitometer are calibrated at the reference temperature condition.

When a densitometer, so calibrated, operates at other temperatures and elevated pressures, the indicated fluid density is calculated first, and then corrected for the above temperature effects characterized at the reference pressure condition and for the above pressure effects characterized at the reference temperature condition. For example:

One form of temperature correction is:

$$D_t = D \cdot (1 + K_{18} \cdot (t - t_0)) + K_{19} \cdot (t - t_0) \quad \text{(Equation 4)}$$

where t is the operating temperature, $t_0$ is the reference temperature and $K_{18}$ and $K_{19}$ are temperature correction coefficient constants. The temperature correction coefficient constants $K_{18}$ and $K_{19}$ are generally calibrated at atmospheric pressure $p_0 = 1$ BarA. If necessary or desired in a complex situation, $K_{18}$ and $K_{19}$ can be expressed as functions of temperature.

One form of pressure correction is:

$$D_p = D_t \cdot (1 + K_{20} \cdot (p - p_0)) + K_{21} \cdot (p - p_0) \quad \text{(Equation 5)}$$

$$K_{20} = K_{20A} + K_{20B} \cdot (p - p_0) + K_{20C} \cdot (p - p_0)^2 \quad \text{(Equation 6)}$$

$$K_{21} = K_{21A} + K_{21B} \cdot (p - p_0) + K_{231C} \cdot (p - p_0)^2 \quad \text{(Equation 7)}$$

where p is the operating pressure, $p_0$ is the reference pressure, and $K_{20A}$, $K_{20B}$, $K_{20C}$, $K_{21A}$, $K_{21B}$ and $K_{21C}$ are pressure correction coefficient constants. The pressure correction coefficient constants $K_{20A}$, $K_{20B}$, $K_{20C}$, $K_{21A}$, $K_{21B}$ and $K_{21C}$ are generally calibrated at a reference temperature $t_0 = 20°$ C. $K_{20}$ and $K_{21}$ can, if necessary or desired, be expanded as higher order polynomial functions of pressure, or expressed as other functions of pressure.

A problem with the above-described calibration is that, at combined elevated pressure and temperature, measurement errors may be observed between the corrected density value $D_p$ and the true density of the fluid under measurement, By way of example, at a combined condition of 80° C. and 100 BarG on a fluid of base density 826.8 kg/m³, the measurement error can be as great as 0.25% or 2 kg/m³. This may exceed the error-acceptance level of many applications, particularly fiscal metering applications.

It is an object of this invention to provide a method of calibrating a vibrating tube densitometer which will go at least some way in addressing the problem described, or which will at least provide a novel and useful addition to the art.

SUMMARY OF THE INVENTION

Accordingly, the invention provides a method of calibrating a vibrating tube densitometer including the steps of:
establishing density coefficients at a reference temperature and pressure condition; establishing temperature effects correction coefficients at the reference pressure condition; and establishing pressure effects correction coefficients at the reference temperature condition;
said method being characterized in that it includes establishing one or more further correction coefficients to compensate for the temperature-pressure coupling effects arising at combined elevated temperature and pressure conditions.

Said further correction coefficients may be determined by calibrating the densitometer using two fluids of densities at substantially the opposite ends of the range of specified densities to be accommodated, each fluid being at a combined elevated temperature and pressure.

Alternatively a single further correction coefficient is derived by calibrating the densitometer using a single fluid of a density substantially at the mid-point of the range of specified densities to be accommodated, said single fluid being at a combined elevated temperature and pressure.

Many variations in the way the invention may be performed will present themselves to those skilled in the art, upon reading the following description. The description should not be regarded as limiting but rather as an illustration, only, of one manner of performing the invention. Where appropriate any element or component should be taken as including any or all equivalents thereof whether or not specifically mentioned.

BRIEF DESCRIPTION OF THE DRAWINGS

One working embodiment of the invention will now be described with reference to the accompanying drawings in which.

DETAILED DESCRIPTION OF WORKING EMBODIMENT

As will be described in greater detail below, the invention provides a method of calibrating a vibrating tube densitometer to take into account the temperature-pressure coupling effects which arise at combined elevated temperatures and pressures.

Figure 1:
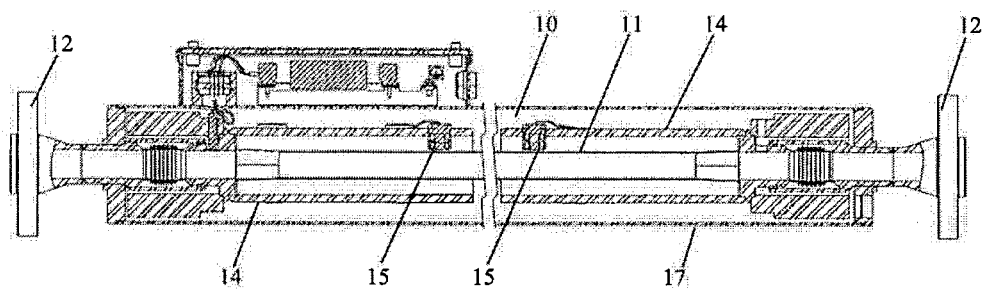
FIG. 1: shows a cross-sectional view of an example of vibrating tube densitometer to which the invention may be applied.

Referring to FIG. 1, a vibrating tube densitometer 10 will be well known to those skilled in the art. A vibrating tube 11 is held between a pair of flanges 12 which, in use, are connected between like flanges on a pipe carrying the fluid whose density is to be measured. Sleeves 14 surround the ends of the tube 11 and carry coils 15 which are located adjacent to the points of maximum lateral displacement of the tube 11 as seen in FIG. 1. In use the coils are powered to cause the tube to vibrate, in the mode shown in FIG. 2, at its natural frequency.

An outer cover 17 is fixed between collars attached to opposite ends of the tube 11.

A more thorough description of this form of apparatus can, for example, be found in British Patent 2 062 865.

Figure 2:
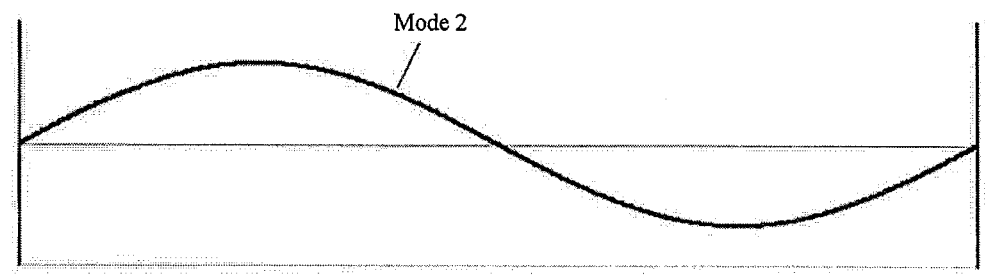
FIG. 2: shows one mode of vibration of the densitometer shown in FIG. 1.

Whilst the description provided herein assumes a lateral mode of vibration shown in FIG. 2, it will be appreciated by those skilled in the art that the general calibration methods herein described are equally applicable to vibrating tube densitometers configured to vibrate in other modes.

Conventionally, vibrating tube densitometers are not calibrated at combined elevated temperature and pressure conditions. By way of example, the density coefficients $K_0$, $K_1$, and $K_2$ mentioned above are determined at reference conditions of 20° C. and 1 BarA; the temperature correction coefficients $K_{18}$ and $K_{19}$ are determined at a reference pressure of 1 BarA; and the pressure correction coefficients $K_{20A}$, $K_{20B}$, $K_{20C}$, $K_{21A}$, $K_{21B}$ and $K_{21C}$ are determined at a reference temperature of 20° C.

The invention proposes methods to calibrate and correct a vibration tube densitometer for the residual temperature-pressure coupling effects at combined elevated temperatures and pressures according to the following expressions:

$$D_{pt}=D_{p'}(1+K_{22}\cdot(t-t_0)\cdot(p-p_0))+K_{23}\cdot(t-t_0)\cdot(p-p_0) \quad \text{(Equation 8)}$$

or:

$$D_{pt}=D_p+(D_p\cdot K_{22}+K_{23})\cdot(t-t_0)\cdot(p-p_0) \quad \text{(Equation 9)}$$

or:

$$D_{pt}=D+K_{pt}\cdot(t-t_0)\cdot(p-p_0) \quad \text{(Equation 10)}$$

in which:

$D_{pt}$ is the final indicated density corrected for temperature-pressure coupling effects, $K_{22}$ and $K_{23}$ are temperature-pressure coupling effects coefficient constants, $K_{pt}=D_p+K_{22}+K_{23}$ is a temperature-pressure coupling effects coefficient on a fluid at measurement conditions.

$K_{22}$ and $K_{23}$ are the coefficients to be calibrated and, generally, $K_{22}$ and $K_{23}$ can be assumed to be constants, i.e. independent of temperature and pressure. In a complex situation $K_{22}$ and $K_{23}$ can be expressed as functions of temperature and pressure.

It has been found that, on a fluid at a given temperature, the temperature-pressure coupling effects correction ($D_{pt}-D_p$) is approximately proportional to the pressure difference ($p-p_0$); and further, that the proportional constant is approximately proportional to the temperature difference ($t-t_0$).

In principle, the temperature-pressure coupling effects coefficient $K_{pt}$ is fluid density dependent, however it has been found that, within a defined limited density range, e.g. ±100 kg/m³, $K_{pt}$ can be approximated to a constant, thus simplifying the calibration.

$K_{22}$ and $K_{23}$ can be determined with the densitometer calibrated on two fluids having densities at the opposite ends of the specified range of densities of interest, each fluid being at an additional combined elevated temperature and elevated pressure condition.

Therefore the following two equations are obtained:

$$D_{pt}(1)=D_p(1)\cdot(1+K_{22}\cdot(t(1)-t_0)\cdot(p(1)-p_0))+K_{23}\cdot(t(1)-t_0)\cdot(p(1)-p_0) \quad \text{(Equation 11)}$$

and $$D_{pt}(2)=D_p(2)\cdot(1+K_{22}\cdot(t(2)-t_0)\cdot(p(2)-p_0))+K_{23}\cdot(t(2)-t_0)\cdot(p(2)-p_0) \quad \text{(Equation 12)}$$

Now let $$C(1)=(t(1)-t_0)\cdot(p(1)-p_0) \quad \text{(Equation 13)}$$

and $$C(2)=(t(2)-t_0)\cdot(p(2)-p_0) \quad \text{(Equation 14)}$$

From Equations 11 and 12, $K_{22}$ and $K_{23}$ can be derived as $$K_{22} = \frac{(D_{pt}(1)\cdot C(2) - D_{pt}(2)\cdot C(1)) - (D_p(1)\cdot C(2) - D_p(2)\cdot C(1))}{(D_p(1) - D_p(2))\cdot C(1)\cdot C(2)} \quad \text{(Equation 15)}$$

and $$K_{23} = \frac{D_{pt}(1) - D_p(1)\cdot(1 + K_{22}\cdot C(1))}{C(1)} \quad \text{(Equation 16)}$$

An alternative approach is to derive a single correction factor $K_{pt}$. Within a limited density range, $K_{pt}$ can be approximated to a constant, therefore simplifying the calibration of the temperature-pressure coupling effects. $K_{pt}$ can be determined by calibrating the densitometer using a single fluid of a density in the middle of the specified range of densities of interest, at an additional combined elevated temperature and elevated pressure condition. Thus the following equation is obtained:

$$D_{pt}=D_p+K_{pt}\cdot(t-t_0)\cdot(p-p_0) \quad \text{(Equation 17)}$$

From Equation 17, $K_{pt}$ can be derived as $$K_{pt} = \frac{D_{pt} - D_p}{(t - t_0)(p - p_0)} \quad \text{(Equation 18)}$$

With more calibration points of the densitometer at multiple combined elevated temperature and pressure conditions, and on multiple fluids, $K_{22}$, $K_{23}$ and $K_{pt}$ can be determined using a least mean square fit method by solving multiple Equations 8, 9 or 10 above.

Calibration

The densitometer is installed on a temperature and pressure controlled rig circulating a first calibration fluid of a known base density. The temperature is set to 20° C., the pressure set to 0 bar gauge and the rig allowed to stabilize. When stabilized, temperature, pressure and densitometer time period readings are recorded.

Whilst maintaining the temperature at 20° C. the pressure is stepped up through to the maximum pressure. At each pressure step the rig is allowed to stabilize before the same set of readings is taken. Typically readings are taken at five pressure points, for example 0, 30, 50, 70 and 100 bar gauge.

Once data has been collected for all pressure readings at 20° C., the system temperature is raised to an elevated temperature, typically 60 or 80° C., and a further set of readings taken at each pressure point (0, 30, 50, 70, 100 bar gauge).

The densitometer is then taken off the rig, cleaned, and then installed on a second, identical, rig circulating a second calibration fluid of a different but known base density. The same calibration steps as described above are then undertaken and the same range of readings obtained.

Next the densitometer is cleaned and mounted to a third rig circulating a third fluid having a base density which differs from that of the first and second fluids. After stabilization a set of readings is taken at 20° C. and at 0 bar gauge. As an alternative to the measurement using this third fluid, a measurement can be taken in air at 20° C. in a temperature controlled area and using barometric pressure to determine the density of air.

The density calibration coefficients are normally referenced to 20° C. and 0 bar gauge. In reality the measurements will not be exactly at 20° C. or 0 bar gauge and so it is not possible to calculate the density coefficients, the temperature coefficients and the pressure coefficients independently from each other. As a consequence the calculation routines usually involve looped calculations and several iterations. Broadly speaking the values of $K_0$, $K_1$ and $K_2$ are calculated from all three calibration fluids (or air in place of the third calibration fluid) at 20° C. and 0 bar; $K_{18}$ and $K_{19}$ are calculated from the first two calibration fluids at 20° C., and at elevated temperature, and 0 bar. $K_{20A}$, $K_{20B}$, $K_{21A}$, $K_{21B}$ and $K_{21C}$ are calculated using the first two calibration fluids at 20° C. and at each pressure point; and $K_{22}$ and $K_{23}$ are calculated using a combination of all the data.

Experimental Results

FIGS. 3 to 7 show comparisons between the current performance with the existing calibration method and the new performance obtained using the alternative methods proposed herein. In all cases density measurement errors are shown at a range of temperature/pressure combinations.

Figure 3:
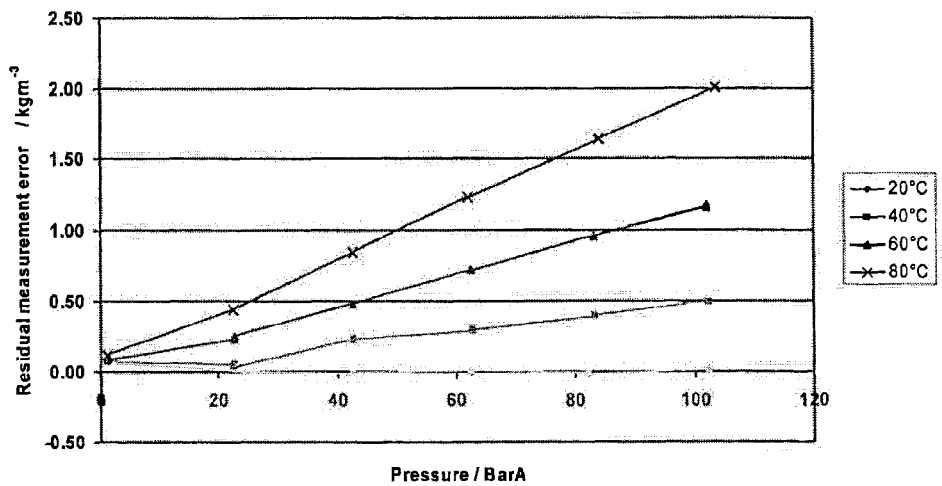
FIG. 3: shows the performance of a vibrating tube densitometer as currently calibrated, on a first fluid.
Figure 4:
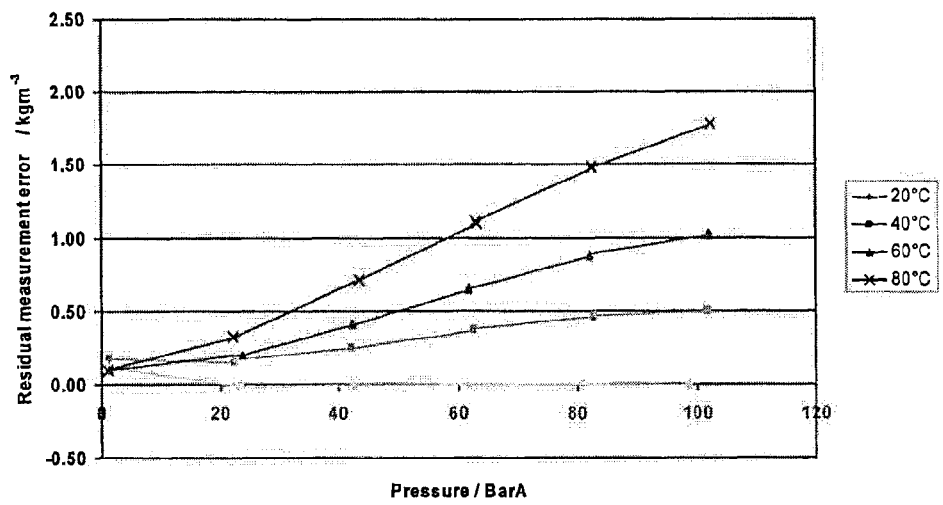
FIG. 4: shows the performance of the same densitometer used in the FIG. 3 example as currently calibrated, on a second fluid.
Figure 5:
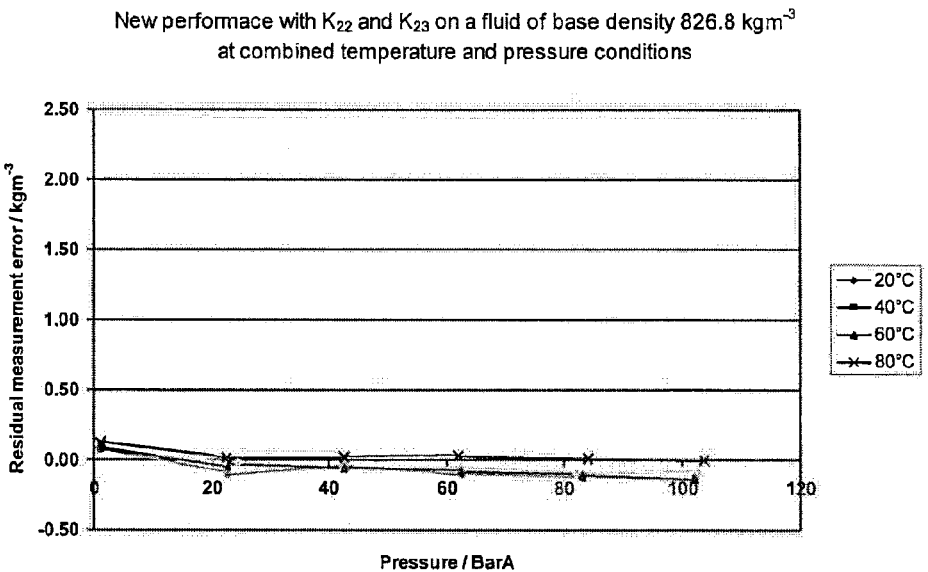
FIG. 5: shows the performance on the first fluid of the densitometer as used in the FIG. 3 example but calibrated in accordance with a first method according to the invention.
Figure 6:
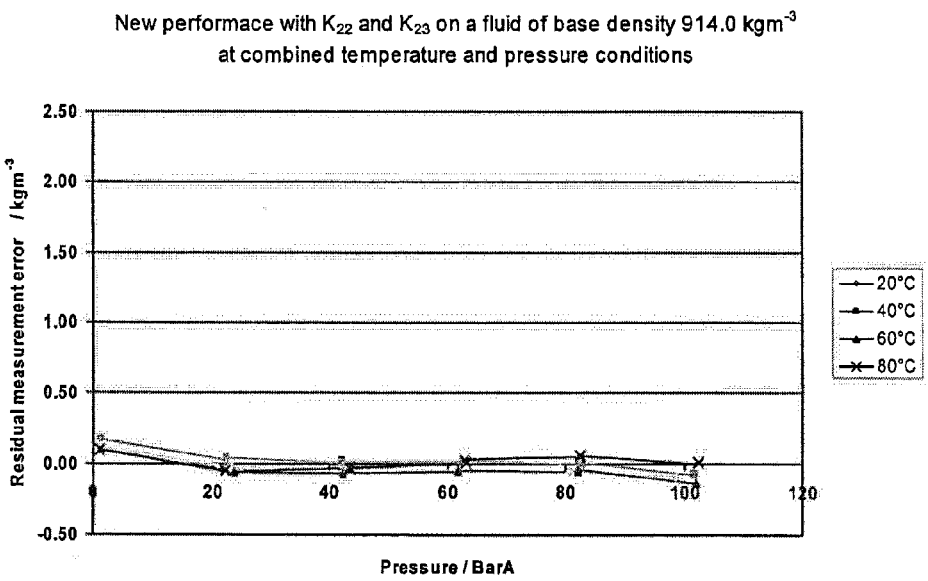
FIG. 6: shows the performance on the second fluid of the densitometer as used in the FIG. 3 example but calibrated in accordance with a first method according to the invention.
Figure 7:
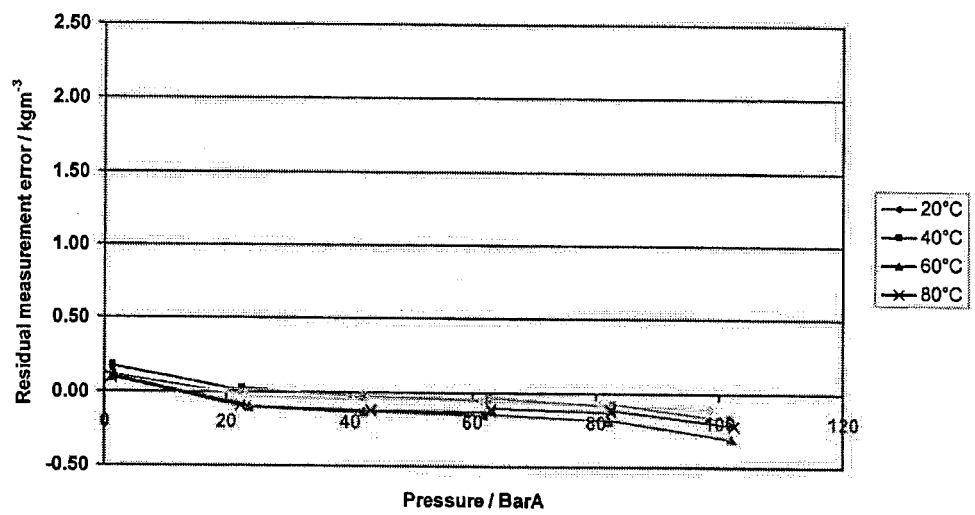
FIG. 7: shows the performance on the second fluid of the densitometer as used in the FIG. 3 example but calibrated on the first fluid in accordance with a second method according to the invention.

The fluid used in the examples shown in FIGS. 3 and 5 has a base density of 826.8 kg/m³ whilst the fluid used in the examples shown in FIGS. 4, 6 and 7 has a base density of 914.0 kg/m³.

It can clearly be seen from FIGS. 3 and 4 that, with no correction for temperature-pressure coupling effects, at combined elevated temperatures and pressures, significant density measurement errors arise.

Referring to FIGS. 5 and 6, by calculating and applying correction coefficients $K_{22}$ and $K_{23}$ in the manner described above, the residual density measurement errors due to temperature-pressure coupling effects are substantially corrected.

FIG. 7 shows the errors of the densitometer on a fluid of base density of 914 kg/m³ with a $K_{pt}$ value calibrated on a fluid of base density 826.8 kg/m³ according to the second or alternative method described above. It can be seen that the residual density measurement errors due to temperature-pressure coupling effects are also substantially corrected.

In relation to the FIG. 7 example, it should be pointed out that, since only two calibration fluids were available, we were able to demonstrate that if the $K_{pt}$ value is calibrated at a density of 826.8 kg/m3 (i.e. this is adopted as the middle value) the resulting $K_{pt}$ value obtained is applicable to a fluid of density as high as 914.0 kg/m3, as tested.

As can be seen, both methods yield much smaller density measurement errors at a temperature and pressure combination of 80° C. and 101 barA, compared with the errors of 2.0 kg/m³ and 1.8 kg/m³, which arise with the same fluids of base density 826.8 kg/m³ and 914.0 kg/m³ respectively, at the same temperature/pressure combination, when calibrated according to current practice.

Thus with the method proposed in the invention, densitometer measurement performance is significantly improved from its current performance at combined elevated temperature and pressure conditions.

The invention claimed is:

1. A vibrating tube densitometer calibrated in accordance with a method, wherein:
   density correction coefficients are established at a reference temperature and pressure condition and are combined with a time period of oscillation measurement to give an uncorrected density value D;
   temperature effects correction coefficients are established at a reference pressure condition and are combined with a temperature measurement to modify the uncorrected density value D to obtain a temperature corrected density value $D_t$;
   pressure effects correction coefficients are established at a reference temperature condition and are combined with a pressure measurement to modify said temperature corrected density value $D_t$ to obtain a pressure corrected density value $D_p$:
   establishing one or more further correction factors to compensate for temperature-pressure coupling effects arising at a combination of elevated temperature and elevated pressure, said one or more further correction factors being combined with said measurements of temperature and pressure to modify said pressure corrected density value $D_p$ to thereby obtain a temperature-pressure coupling effects corrected density value $D_{pt}$, wherein said one or more further correction factors are determined by calibrating the densitometer using two fluids of densities at substantially the opposite ends of the range of specified densities to be accommodated, each fluid being at a combined elevated temperature and pressure.

2. A vibrating tube densitometer calibrated in accordance with a method, wherein:
   density correction coefficients are established at a reference temperature and pressure condition and are combined with a time period of oscillation measurement to give an uncorrected density value D;
   temperature effects correction coefficients are established at a reference pressure condition and are combined with a temperature measurement to modify the uncorrected density value D to obtain a temperature corrected density value $D_t$;
   pressure effects correction coefficients are established at a reference temperature condition and are combined with a pressure measurement to modify said temperature corrected density value $D_t$ to obtain a pressure corrected density value $D_p$:
   establishing one or more further correction factors to compensate for temperature-pressure coupling effects arising at a combination of elevated temperature and elevated pressure, said one or more further correction factors being combined with said measurements of temperature and pressure to modify said pressure corrected density value $D_p$ to thereby obtain a temperature-pressure coupling effects corrected density value $D_{pt}$, wherein a single further correction coefficient is derived by calibrating the densitometer using a single fluid of density substantially at the mid-point of the range of specified densities to be accommodated, said single fluid being at a combined elevated temperature and pressure.

* * * * *